United States Patent [19]

Lombardino

[11] Patent Number: 4,567,179
[45] Date of Patent: Jan. 28, 1986

[54] ANTIINFLAMMATORY SALTS OF PIROXICAM

[75] Inventor: Joseph G. Lombardino, Niantic, Conn.

[73] Assignee: Pfizer, Inc., New York, N.Y.

[21] Appl. No.: 659,733

[22] Filed: Oct. 11, 1984

[51] Int. Cl.$^4$ ............... C07D 279/02; C07D 417/02; A61K 31/54
[52] U.S. Cl. ........................................ 514/225; 544/49
[58] Field of Search ........................... 544/49; 514/225

[56] References Cited

U.S. PATENT DOCUMENTS 4,230,717  10/1980  Brown et al. .................. 424/274

FOREIGN PATENT DOCUMENTS 2105193  3/1983  United Kingdom .
2105588  3/1983  United Kingdom .

OTHER PUBLICATIONS

The Merck Index, 10th Edition, pp. 499, 750, 1080, 1082–1083, 1151–1152 & 1386, (1983).
Fielding et al., Eur. Surg. Res. 9, 252, (1977).
Kasuya et al., Japan J. Pharmacol. 29, 670, (1979).
McGreevy et al., Surg. Forum 28, 357, (1977).
Ruud et al., Curr. Med. Res. Opin. 6 (Suppl. 9), 37, (1980).
Hoff et al., Scand. J. Gastroent. 16, 1041, (1981).
Leitold et al., Arch. Pharmacol 6 (Suppl), R50, (1981).
Leitold et al., Advances in Experimental Ulcer, Umehara and Ito, editors, ICEU, Tokyo, 1984, pp. 27–36.
Leitold et al., Arzneim. Forsch./Drug Res. 34, 468, (1984).
"Flexicamino B$_{12}$" Promotional Literature.
Okabe et al., Am. J. Dig. Dis. 22, pp. 677–684, (1977).
Brown et al., Eur. J. Pharmacol. 51, pp. 275–283, (1978).
Hayden et al., J. Pharm. Pharmacol. 30, pp. 244–246, (1977).
Djahanguiri et al., Eur. J. Pharmacol. 51, pp. 77–79, (1978).
Takeda et al., Arzneim-Forsch 32, pp. 734–737, (1982).
Croker et al., Ann. Rheum. Dis. 39, pp. 275–278, (1980).
Schumacher et al., Am. J. Clin. Nutr. 28, 1200, (1975).
Lindenbaum et al., Nutr. Metabol. 17, 368, (1974).
Lemeshko et al., Sov. Med. 29, 33, (1966).
Dovgyallo et al., Klin. Med. (Mosk) 51, 57, (1973).
Litinskaya Vrech. Delo. 1977, 93.
"Rote Liste 1981" Abstracts 05-216 to 239, 265–284, 334–348, 407–459.
Gerhold, Fortsch. Therapy, 92 Supplement, pp. 1–4, (1974).
Pietrogrande et al., Clin. Ter. 71, pp. 531–537, (1974).

*Primary Examiner*—John M. Ford
*Attorney, Agent, or Firm*—Charles J. Knuth; Albert E. Frost; Robert K. Blackwood

[57] ABSTRACT

Improved antiinflammatory salts of piroxicam with antidepressant doxepin, with bronchodilator pirbuterol or isoproterenol, with H$_2$-antagonist inhibitor 2-guanidino-4-(2-methyl-4-imidazolyl)thiazole, with pyridoxine, a member of the vitamin B$_6$ complex, or with antihypertensive trimazosin.

12 Claims, No Drawings

ANTIINFLAMMATORY SALTS OF PIROXICAM

BACKGROUND OF THE INVENTION

The present invention is concerned with improved antiinflammatory salts of piroxicam treating inflammation therewith. These salts are composed of piroxicam in 1:1 molar ratio with antidepressant doxepin, bronchodilator pirbuterol or isoproterenol, histamine-$H_2$ antagonist 2-guanidino-4-(2-methyl-4-imidazolyl)thiazole, with pyridoxine or another member of the vitamin $B_6$ complex such as pyridoxal or pyridoxamine, or with antihypertensive trimazosin or structurally related antihypertensive compound. The generic names used here and elsewhere herein are from the USAN and the USP Dictionary of Drug Names, 1961–1981, Griffiths et al., ed., U.S. Pharmacopeial Convention Inc., Rockville, Md., 1984, have subsequently been assigned and published as official USAN names, and/or appear in The Merck Index 10th Edition. Alternative chemical names which are provided in The Merck Index are listed below.

Gastrointestinal irritation, including ulcers, is a side effect commonly associated, to one degree or another, with antiinflammatory agents. In many cases, individuals requiring such antiinflammatory treatment are precluded from enjoying the benefits thereof because of their susceptibility to such side effects. The present salts of piroxicam with one or another medicinal agent, as defined above, permit desirable antiinflammatory therapy while preventing or ameliorating said gastrointestinal irritation or ulcers.

Bronchodilators salbutamol (albuterol), phenylephrine and isoproterenol, but not propranolol, have been reported to inhibit formation of indomethacin-induced ulcers in animals [Fielding et al., Eur. Surg. Res. 9, 252 (1977); Kasuya et al., Japan J. Pharmacol. 29, 670 (1979)]. In another study, administration of isoproterenol to a chambered section of a dog's fundus reduced or prevented aspirin-induced tissue damage [McGreevy et al., Surg. Forum 28, 357 (1977)]. There are no known prior reports concerning the effect of bronchodilator pirbuterol on antiinflammatory agents.

Antidepressant doxepin has also been reported to have gastric antisecretory activity and to be as effective as cimetidine in the treatment of duodenal ulcers in humans [Hoff et al., Curr. Med. Res. Opin. vol. 6, supplement 9, page 36 (1980); Scand. J. Gastroent. 16, 1041 (1981)]. It has also been reported that doxepin shows antiulcer and antisecretory activity in rats and dogs; and that it significantly reduced the ulcerogenic potential of indomethacin, diclofenac and aspirin in water-immersion restraint-stressed rats [Leitold et al. Arch. Pharmacol. 316 (supplement), R50, abstract 199 (1981); Leitold et al., Advances in Experimental Ulcer, Umehara and Ito, editors, ICEU, Tokyo pp. 27–36 (1982); Arzneim-Forsch/Drug Res. 34, 468 (1984).

Histamine-$H_2$ antagonist (gastric acid antisecretory, antiulcer) compounds such as ranitidine, cimetidine and 1-methyl-5-[[3-[3-(1-piperidinylmethyl)phenoxy]-propylamino]]-1H-1,2,4-triazole-3-methanol have been previously physically combined with indomethacin, piroxicam and other antiinflammatory agents to decrease gastric irritation. See, for example, U.K. patent application Nos. 2,105,193 and 2,105,588; and Lovelace, U.S. Pat. No. 4,230,717.

There are no known literature reports concerning the use of an antihypertensive agent such as trimazosin, a vitamin such as pyridoxine or a minor tranquilizer such as diazepam in reducing gastric side-effects induced by nonsteroidal antiinflammatory agents.

Concurrently filed U.S. patent application Ser. No. 659,602 by Crawford et al. describes the combination of piroxicam (or a pharmaceutically-acceptable salt) with either doxepin, trimazosin, pyridoxine or pirbuterol (or their pharmaceutically-acceptable salts) in improved antiinflammatory compositions and methods. Concurrently filed U.S. patent application Ser. No. 659,752 by LaMattina describes such a combination of piroxicam with 2-guanidino-4-(2-methyl-4-imidazolyl)thiazole.

SUMMARY OF THE INVENTION

The present invention concerns improved antiinflammatory salts of piroxicam as defined above and an improved method for the treatment of inflammation which comprises treatment with an antiinflammatory amount of one of said piroxicam salts.

DETAILED DESCRIPTION OF THE INVENTION

The antiinflammatory component of the salts of the present invention, piroxicam, is known. For example, The Merck Index 10th Ed., 1983 contains a monograph concerning piroxicam (no. 7378), as does the Physicians' Desk Reference (PDR), 38th Ed., pp. 1556–1557 (1984). The ethanolamine salt of piroxicam is disclosed in U.S. Pat. No. 4,434,164. As listed in The Merck Index, alternative chemical names for piroxicam are 4-hydroxy-2-methyl-N-2-pyridinyl-2H-1,2-benzothiazine-3-carboxamide 1,1-dioxide and 3,4-dihydro-2-methyl-4-oxo-N-2-pyridyl-2H-1,2-benzothiazine-3-carboxamide 1,1-dioxide.

The other component of the salts of the present invention are also known compounds. Doxepin is an antidepressant, marketed in the form of its hydrochloride salt (The Merck Index 10th Ed., monograph no. 3434; PDR 38th Ed., pp. 1688–1689; alternatively named in The Merck Index as 3-dibenz[b,e]oxepin-11(6H)-ylidene-N,N-dimethyl-1-propanamine and as N,N-dimethyldibenz[b,e]oxepin-$\Delta$11(6H), $\alpha$-propylamine). Isoproterenol is a known bronchodilator (The Merck Index 10th Ed., monograph No. 5065; PDR 38th Ed., pp. 715–718; alternatively named in The Merck Index as 4-[1-Hydroxy-2-[1-methylethyl)amino]ethyl]-1,2-benzenediol and as 3,4-dihydroxy-$\alpha$-[(isopropylamino)methyl]benzyl alcohol). Pirbuterol is a bronchodilator marketed in the form of its dihydrochloride and monoacetate salts. See The Merck Index 10th Ed., monograph no. 7364. The Merck Index alternatively names pirbuterol as —$\alpha^6$[[(1,1-dimethylethyl)amino]methyl]-3-hydroxy-2,6-pyridinedimethanol and as 2-hydroxymethyl-3-hydroxy-6-(1-hydroxy-2-tert-butylaminoethyl)pyridine. Its early synthesis and utility as a bronchodilator is disclosed in U.S. Pat. Nos. 3,700,681; 3,763,173; 3,772,314 and 3,786,160. Alternative and generally improved syntheses are found in U.S. Pat. Nos. 3,948,919; 4,011,231; and 4,031,108; Luxembourg Pat. No. 79564; and European patent application Nos. 58069, 58070, 58071 and 58072. More recently, pirbuterol has also found utility in the treatment of congestive heart failure (U.S. Pat. No. 4,175,128). Trimazosin (The Merck Index 10th Ed., monograph no. 9506; alternatively named as 4-(4-amino-6,7,8-trimethoxy-2-quinazolinyl)-1-piperazinecarboxylic acid 2-hydroxy-2-methylpropyl ester) is an anti-hypertensive agent, marketed or to be marketed around the world as a hydrochloride salt. It is structurally related to prazosin. Pyridoxine is marketed as its hydrochloride salt as one of the vitamins of the B$_6$ complex (see The Merck Index 10th Ed., monograph no. 7882; alternatively named as 5-hydroxy-6-methyl-3,4-pyridinedimethanol and as pyridoxol).

The clinical value of the present improved salts as improved antiinflammatory agents is reflected by appropriate animal studies. Typically the antiinflammatory activity is determined in the standard carrageenin-induced rat foot edema test [described by C. A. Winter et al., Proc. Soc. Exp. Biol. 111, p. 544 (1962)]. In this test, antiinflammatory activity is determined as the inhibition of edema formation in the hind paw of male albino rats (usual weight 150–190 g.) in response to a subplantar injection of carrageenin. The carrageenin is injected as a 1 percent aqueous suspension (0.05 ml.) 1 hour after oral administration of the drug. Edema formation is then assessed 3 hours after the carrageenin injection by measuring the volume of the injected paw initially as well as at the 3 hour mark. The increase in volume three hours after carrageenin injection constitutes the individual response. Compounds are considered active if the response between the drug-treated animals (six rats/group) and the control group (i.e., animals receiving the vehicle alone) is deemed to be significant on comparison with results afforded by standard compounds like acetylsalicylic acid at 100 mg./kg or phenylbutazone at 33 mg/kg., both by the oral route of administration. The antiinflammatory activity of the present salts is generally consistent with the piroxicam content of each individual salt.

The clinical activity of the instant salts against rheumatoid arthritis is also reflected by their efficacy against adjuvant-induced arthritis in rats. In this test adjuvant arthritis is typically induced in adult male Wistar-Lewis rats weighing 250–270 grams each (Charles River Breeding Laboratories, Kingston, N.Y.) by a single subplantar injection of 1 mg of *Mycobacterium butyricum* (Difco Laboratories, Lot #0640-33) suspended in 0.1 ml mineral oil as described by Walz et al. (Proc. Soc. Exptl. Biol. Med., 136: 907–910, 1971). Seven rats are used in each group. The salts are usually orally administered in water at near-neutral pH, obtained by neutralization with dilute HCl or NaOH if necessary. A volume of 10 ml/kg body weight is generally given by intubation with a blunt end, 18-gauge needle, with multiple doses of each drug given starting 1 day before the injection of adjuvant and continuing until 16 days after the induction of the arthritic lesion. The initial hindpaw volumes (Vi) are measured on the day of adjuvant injection and the resultant swelling was determined on the injected paw (Vf - Vi) on the 4th day following the adjuvant injection. This was considered to be the primary response or lesion. The swelling (Vf - Vi) measured 16 days after adjuvant injection on the contralateral, non-injected hindpaw constituted the secondary response or lesion. The rats are weighed at the start of the experiments as well as 4 and 16 days after the induction of the disease. Percent inhibition of edema is calculated according to the following formula:

% Inhibition of Edema =

$$1 - \left[ \frac{Vf \text{ drug} - Vi \text{ drug}}{Vf \text{ control} - Vi \text{ control}} \right] \times 100$$

In these tests, the activity of the salt is generally at least equivalent to that of the contained piroxicam.

The improved nature of the present salts lies primarily in the reduced ability to induce gastric irritation, again demonstrated by testing in rats. The salts are generally dosed in rats at a level which will provide the molar equivalent of 100 mg/kg. of piroxicam, based on the calculated piroxicam content of each salt. At this high level piroxicam and its non-medicinal, pharmaceutically-acceptable salt will induce a significant level of gastric lesions. Typically adult male "specific pathogen free" rats weighing 140–160 grams of the CD strain (Sprague-Dawley), obtained from Charles River Breeding Laboratories (Kingston, N.Y.), are acclimated for approximately one week and tested when they reached a body weight of 200–225 grams. The rats are fasted for 16 hours and randomized into groups consisting of 7 to 20 animals which are normalized with regard to their average body weight. Gastric ulcers are induced in the animals by orally dosing them with a single dose of salt equivalent to about 100 mg/kg of piroxicam dissolved or suspended in 2 ml. of aqueous 0.1% methylcellulose. Six and one-half hours later, the animals are sacrificed by cervical dislocation and autopsied. The stomachs are surgically removed, dissected along the greater curvature and rinsed with cold water. The stomachs are individually scored for both linear and punctate lesions. The total number of lesions is used for scoring purposes. The data obtained from each group of rats is analyzed and compared to the controls per se, in the form of its free acid or as a non-medicinal pharmaceutically-acceptable salt. Based on equivalent piroxicam content, the salts of the present invention show a reduced level of gastric lesions over said piroxicam per se. For example, a control group of 20 animals receiving a dose of 120 mg/kg. of the ethanolamine salt demonstrated a mean value of $9.0\pm1.0$ lesions per rat stomach, while a second group of 20 receiving 200 mg/kg of the 2-guanidino-4-(2-methyl-4-imidazolyl)thiazole salt of piroxicam demonstrated only $2.5\pm0.7$ lesions/rat.

The present invention is readily carried out. The piroxicam salt is dosed in a range equivalent to 0.1 to 1 mg of piroxicam/kg/day. The second medicinal agent will of course be present in equimolar quantity, 0.1 to 1 mg of piroxicam corresponding to:

0.084 to 0.84 mg of doxepin;
0.073 to 0.73 mg of pirbuterol;
0.064 to 0.64 mg of isoproterenol;
0.067 to 0.67 mg of 2-guanidino-4-(2-methyl-4-imidazolyl)thiazole;
0.131 to 1.31 mg of trimazosin; or
0.048 to 0.48 mg of pyridoxine; reflecting the respective molecular weight ratios.

In the preferred oral route of dosage, the preferred amount of salt will generally be in the range equivalent to 5–50 mg/day of free piroxicam/adult patient, thereby providing molar equivalent amounts of the second medicinal agent as follows:
4.2 to 42 mg/day of doxepin;
3.62 to 36.2 mg/day of pirbuterol;
3.19 to 31.9 mg/day of isoproterenol;

3.35 to 33.5 mg/day of 2-guanidino-4-(2-methyl-4-imidazolyl)thiazole;
6.57 to 65.7 mg/day of trimazosin; or
2.55 to 25.5 mg/day of pyridoxine;
an amount of the second medicinal agent generally sufficient to inhibit gastrointestinal side effects which might otherwise have been induced by the piroxicam in patients susceptible to such side effects.

The present salts are administered alone or in further combination with pharmaceutically-acceptable carriers or diluents. For oral use, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. Thus, for oral administration, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

The present invention is illustrated by the following examples. However, it should be understood that the invention is not limited to the specific details of these examples.

EXAMPLE 1

The 1:1 Doxepin Salt of Piroxicam

Under nitrogen, piroxicam (1.66 g., 0.005 mol) was partially dissolved in 60 ml. $CH_3OH$. Doxepin (1.40 g., 0.005 mol) in 40 ml. $CH_3OH$ was added, resulting in a clear solution within 1 minute. The mixture was stirred 15 minutes, then evaporated to dryness in vacuo to yield title product as a free-flowing, yellow powder, 2.58 g., after removal from the pot and drying at 45° C. in vacuo; m.p. 115°–117° C.; ir (KBr) includes amide NH peak at 2.93 microns, N+H peak at 3.3 microns (absent in a physical mixture of piroxicam and doxepin), amide carbonyl at 6.05 microns and $SO_2$ at 7.55 and 8.55 microns.

Anal. Calcd. for $C_{34}H_{34}O_5N_4S$: C, 66.87; H, 5.61; N, 9.17. Found: C, 66.84; H, 5.67; N, 9.10.

EXAMPLE 2

The 1:1 Pyridoxine Salt of Piroxicam Pyridoxine (3.38 g., 0.02 mol) is dissolved in 100 ml. $CH_3OH$. Piroxicam (6.63 g., 0.02 mol) is dissolved in 100 ml. $CH_2Cl_2$ and the pyridoxine solution added. The resulting solution is evaporated in vacuo to yield title product.

EXAMPLE 3

The 1:1 2-Guanidino-4-(2-methyl-4-imidazolyl)thiazole Salt of Piroxicam

Piroxicam (0.994 g., 0.003 mol) was suspended in 20 ml. $CH_3OH$. 2-Guanidino-4-(2-methyl-4-imidazolyl)-thiazole (0.667 g., 0.003 mole) in 25 ml. $CH_3OH$ was added and the suspension stirred for 75 minutes as the mixture remained as a slurry without visible change. The mixture was heated to reflux for 10 minutes, resulting in a clear solution within 2 minutes. The mixture was cooled to room temperature, clarified by filtration (removing 120 mg. of white solids) and the mother liquor evaporated to dryness in vacuo to yield title product as a free flowing powder, 1.30 g., after removal from the flask and drying at 45° C. under high vacuum; m.p. 182° C. with decomposition; ir (KBr) includes broad band in 2.90–4.3 micron region (multiple NH plus $H_2O$); 5.87 microns (amide carbonyl) and 7.52 and 8.55 microns ($SO_2$).

Anal. Calcd. for $C_{23}H_{23}O_4N_9S_2.0.75H_2O$: C, 48.71; H, 4.35; N, 22.22. Found: C, 48.53; H, 4.38; N, 22.47.

EXAMPLE 4

The 1:1 Pirbuterol Salt of Piroxicam

Under $N_2$, a clarified solution of pirbuterol (2.35 g., 0.0096 mol) in 25 ml. $CH_3OH$ was added to a slurry of piroxicam (3.17 g., 0.0096 mol) in 50 ml. of $CH_3OH$, forming a nearly clear solution which, after stirring for 20 minutes, was clarified by filtration and evaporated to dryness in vacuo to yield, after removal from the flask and drying in a dessicator over $P_2O_5$ under high vacuum for 20 hours, 5.52 g. of title product; m.p. 98° C. with decomposition. A small portion of this material when dried at 58° C. for 16 hours under high vacuum melted at m.p. 122° C. with decomposition.

Anal. Calcd. for $C_{27}H_{33}O_7N_5S.H_2O$: C, 55.00; H, 5.98; N, 11.87. Found: C, 54.66; H, 5.92; N, 11.74.

The bulk of the above material (5.20 g.) was dried down to 4.90 g. by drying under high vacuum at 73° C. for 66 hours; ir (KBr) includes broad peak 2.75–4.2 microns ($NH_2^+$), 6.12 microns (amide carbonyl) and 7.58 and 8.55 microns ($SO_2$).

Anal. Calcd. for $C_{27}H_{33}O_7N_5S.H_2O$: C, 55.00; H, 5.98; N, 11.87. Found: C, 55.25; H, 5.63; N, 11.97.

Additional product (0.27 g.) was obtained by slurry of the residue in the flask with 5 ml. of ethyl acetate, filtration and drying at 73° C. for 66 hours under high vacuum.

In each case, the product was a free flowing, readily handled powder.

EXAMPLE 5

1:1 Isoproterenol Salt of Piroxicam

Under nitrogen, piroxicam (3.86 g., 0.0116 mol) was slurried in 50 ml. $CH_3OH$. Isoproterenol (2.46 g., 0.0116 mol) was partially dissolved in 100 ml. of $CH_3OH$ and the slurry added to the piroxicam slurry. After stirring for 20 minutes, the resulting clear solution was evaporated to dryness to yield title product as a free flowing, easily handled powder, 6.20 g., after removing from the flask and drying under high vacuum for 66 hours; m.p. 108° C. with decomposition; ir (KBr) includes broad peak at 2.78 to 4.3 microns (NH and $H_2O$), 6.15 microns (amide carbonyl) and 7.55 and 8.57 microns ($SO_2$).

Anal. Calcd. for $C_{26}H_{30}O_7N_4S.2H_2O$: C, 53.97; H, 5.92; N, 9.68. Found: C, 54.22; H, 5.30; N, 9.80.

EXAMPLE 6

The 1:1 Trimazosin Salt of Piroxicam

Trimazosin (free base; 4.70 g., 0.01 mol) was suspended in 200 ml. $CH_3OH$ and added to a suspension of piroxicam (3.31 g., 0.01 mol) in 100 ml. $CH_3OH$. On stirring, the color changed to pale yellow and partial solution occurred. After one hour, the latter was warmed to 65° C. with stirring for 30 minutes. The resulting clear solution was cooled to room temperature, clarified by filtration to remove trace insoluble material, evaporated to solids in vacuo, and the product dried at 60° C. over P$_2$O$_5$; 6.84 g. (89%); m.p. 162°–164° C.

Anal. Calcd. for C$_{35}$H$_{42}$O$_{10}$N$_8$S: C, 54.82; H, 5.52; N, 14.61. Found: C, 54.54; H, 5.37; N, 14.55.

PREPARATION 1

Doxepin

Doxepin hydrochloride (10 g., 0.032 mol) was dissolved in 50 ml. H$_2$O. Sodium bicarbonate (3.2 g., 0.038 mol) suspended in 25 ml. of H$_2$O was added with stirring, and the mixture stirred for 20 minutes and then extracted 3×50 ml. ether. The ether extracts were combined, dried (Na$_2$SO$_4$) and evaporated in vacuo to yield doxepin as an oil (8.33 g.).

PREPARATION 2

Pirbuterol

Under nitrogen, pirbuterol dihydrochloride (3.0 g., 0.0096 mol) was dissolved in 10 ml. CH$_3$OH. KOH (85%, 1.3 g., 0.0197 mol) in 30 ml. of CH$_3$OH was added dropwise over 10 minutes. After stirring 30 minutes, precipitated KCl (1.25 g.) was removed by filtration and the mother liquor evaporated to a white foam, 2.56 g. The latter was taken up in 20 ml. 1:1 acetone:CH$_3$OH and allowed to stand 18 hours. Additional KCl (0.09 g.) was recovered by filtration and the mother liquor evaporated in vacuo to yield title product, dried under high vacuum, 2.35 g.

PREPARATION 3

Isoproterenol

By the method of the preceding Preparation, isoproterenol hydrochloride was converted to title product, 2.46 g.

PREPARATION 4

2-Guanidino-4-(2-methyl-4-imidazolyl)thiazole Dihydrobromide

Method A

2-Methyl-4-acetylimidazole (4.00 g, 0.0322 mol; U.S. Pat. No. 4,374,843) was dissolved in 48% HBr (40 ml, 0.351 mol), the temperature rising to 33° C. The solution was heated to 50° C. Br$_2$ (1.65 ml, 5.15 g, 0.0322 mol) in 5 ml of 48% HBr was added dropwise over 17 minutes maintaining that temperature with external heating as necessary. The stirred reaction mixture was heated to 65° C. for 1.5 hours, cooled and stripped to a cream-colored slurry. The mixture was chased 2×20 ml H$_2$O (the solids dissolving and returning to a thick slurry each time). Without further isolation of the intermediate 2-methyl-4-(bromoacetyl)imidazole, absolute ethanol (29.2 ml) was added, and then N-amidinothiourea (3.81 g, 0.0322 mol) and the slurry heated to reflux. The resulting solution was refluxed for 2 hours, by which time there was heavy precipitation of crystalline title product. The slurry was distilled to half-volume, cooled to room temperature, and title product recovered by filtration with a small amount of ethanol wash and dried at 35° C. in vacuo; 10.12 g (79% over two chemical steps); homogeneous by tlc Rf 0.75 (19:1 ethanol:concentrated NH$_4$OH); m.p. 300° C. (decomposition).

Analysis calculated for C$_8$H$_{10}$N$_6$S.2HBr.0.5H$_2$O: C, 24.44; H, 3.33; N, 21.38%. Found: C, 24.20; H, 3.18; N, 21.43%.

Method B

In the manner of Method A, 2-methyl-4-acetylimidazole (4.00 g, 0.0322 mol) was brominated, but with substitution of 3.67 ml (0.0322 mol) of 48% HBr and 4 ml of acetic acid for the initial charge of 48% HBr, and charging the Br$_2$ (1.65 ml) in 4 ml of acetic acid in place of 48% HBr. At the end of the 1.5 hour heating period (without cooling, stripping and chasing), the N-amidinothiourea (3.81 g) was added. The reaction exothermed from 67° to 77° C., and the resulting solution was heated at 80° C. for 1 hour during which title product began to precipitate heavily. Title product was recovered as in Method A, 9.34 g (73% over two chemical steps), identical with the product of Method A.

Method C

To 48% HBr (16.9 ml) was added 2-methyl-4-acetylimidazole (7.36 g, 0.059 mol) to form a clear yellow solution. Br$_2$ (3.0 ml, 0.059 mol) in 48% HBr (3.3 ml) was added dropwise as the reaction was warmed to 45° C. Transient precipitation was noted during addition and heating. After stirring for 18 hours at 45° C., the reaction mixture was cooled to 30° C., diluted with 22 ml absolute ethanol, and N-amidinothiourea (7.0 g) was added. The resulting slurry almost became clear, then set up to solids which were broken up with a spatula. The resulting mobile slurry was stirred at 55° C. for 2 hours, cooled to 10° C., and title product recovered by filtration with 2×5 ml absolute ethanol wash, 20.3 g (86%), identical with title product of Method A.

PREPARATION 5

2-Guanidino-4-(2-methyl-4-imidazolyl)thiazole (Free Base)

2-Guanidino-4-(2-methyl-4-imidazolyl)thiazole dihydrobromide (13.4 g) was stirred with 66.9 ml H$_2$O and the pH slowly adjusted to a stable value of 10.0 over 2 hours with 22.6 ml of 3N NaOH while maintaining a temperature of 22°–24° C. Title product was recovered by suction filtration with water wash, pulled to a tight cake under a rubber dam, repulped in 28 ml acetone for 2 hours, refiltered, washed with 12 ml acetone and dried at 40° C. in vacuum to yield crystalline title product, 8.66 g, containing about 15% water.

Anhydrous free base was prepared from water-wet cake (prepared as above, without acetone repulp) by dissolving 4.04 g of the water-wet cake (estimated to contain 1.60 g of free base on a dry basis) in 80 ml of refluxing acetone, treating the solution with 0.16 g activated carbon, filtering hot, concentrating the filtrate to 15 ml, stirring at room temperature for 1 hour, filtering with acetone wash and drying the cake at 40° C. in vacuo; yield: 1.57 g.

I claim:
1. A 1:1 doxepin salt of piroxicam.
2. A method of treating inflammation in a mammal which comprises administering to said mammal an antiinflammatory amount of the salt of claim 1.
3. A 1:1 pyridoxine salt of piroxicam.
4. A method of treating a mammal which comprises administration to said mammal an antiinflammatory amount of the salt of claim 3.
5. A 1:1 2-guanidino-4-(2-methyl-4-imidazolyl)-thiazole salt of piroxicam.

6. A method of treating inflammation in a mammal which comprises administration to said mammal an antiinflammatory amount of the salt of claim 5.

7. A 1:1 pirbuterol salt of piroxicam.

8. A method of treating inflammation in a mammal which comprises administration to said mammal an antiinflammatory amount of the salt of claim 7.

9. A 1:1 isoproterenol salt of piroxicam.

10. A method of treating inflammation in a mammal which comprises administration to said mammal an antiinflammatory amount of the salt of claim 9.

11. A 1:1 trimazosin salt of piroxicam.

12. A method of treating inflammation in a mammal which comprises administration to said mammal an antiinflammatory amount of the salt of claim 11.

* * * * *